US007001338B2

(12) United States Patent
Hayek et al.

(10) Patent No.: US 7,001,338 B2
(45) Date of Patent: Feb. 21, 2006

(54) SYSTEM AND METHOD FOR DIAGNOSING PATHOLOGIC HEART CONDITIONS

(75) Inventors: Carleton S. Hayek, Ellicott City, MD (US); W. Reid Thompson, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 164 days.

(21) Appl. No.: 10/808,196

(22) Filed: Mar. 24, 2004

(65) Prior Publication Data

US 2004/0193067 A1  Sep. 30, 2004

Related U.S. Application Data

(60) Provisional application No. 60/457,726, filed on Mar. 26, 2003.

(51) Int. Cl.
*A61B 5/02* (2006.01)
(52) U.S. Cl. .................. 600/528; 600/508; 600/514
(58) Field of Classification Search ............... 600/528, 600/512, 514, 508
See application file for complete search history.

(56) References Cited

U.S. PATENT DOCUMENTS

| | | | |
|---|---|---|---|
| 4,428,381 A | | 1/1984 | Hepp |
| 4,458,693 A | | 7/1984 | Badzinski et al. |
| 5,012,815 A | | 5/1991 | Bennett, Jr. et al. |
| 5,301,679 A | | 4/1994 | Taylor |
| 5,638,823 A | * | 6/1997 | Akay et al. .................. 600/528 |
| 5,687,738 A | | 11/1997 | Shapiro et al. |

(Continued)

FOREIGN PATENT DOCUMENTS

| WO | WO 99/52436 | 10/1999 |
|---|---|---|
| WO | WO 02/096293 | 12/2002 |

OTHER PUBLICATIONS

"Automatic Detection of Sounds and Murmurs in Patients with Ionescu-Shiley Aortic Bioprostheses", Baranek, H.L., et al., Medical and Biological Engineering and Computing, Sep. 1989, pp. 449-455.

*Primary Examiner*—Robert E. Pezzuto
*Assistant Examiner*—Brian T. Gedeon
(74) *Attorney, Agent, or Firm*—Francis A. Cooch

(57) ABSTRACT

A method of diagnosing pathologic heart conditions in which a time series of heart sounds is filtered and parsed into a sequence of individual heart cycles. A systolic interval as well as systolic sub-intervals are identified for each heart cycle. The systolic intervals and ECG peaks are then digitally filtered to optimize for click detection. For each heartcycle, systole time limits are determined, a time series of the transform at specific wavelet scales are input to a Neyman-Pearson "constant false alarm rate" (CFAR) detector to identify anomalously high wavelet coefficients, and a vector of detections vs. time is created. The series of anomalously high detections (one series for each heart cycle) are then assembled into a matrix and convolved with an averaging vector yielding detection statistics across heart cycles and time intervals consistent with an observed spread of click occurrence times. A click score is then determined as the maximum element of the vector formed by the median wavelet coefficient amplitude across heart cycles squared at each time sample multiplied element-wise by the vector formed by the sum across heart cycles of the number of detections at each time sample. The click score is compared to a threshold value set by a desired probability of detection vs. a probability of false alarm tradeoff. If the click score is less than the threshold then a "no click" indicator is displayed. If the click score is greater than the threshold then a "click present" indicator is displayed.

30 Claims, 3 Drawing Sheets

U.S. PATENT DOCUMENTS

| | | |
|---|---|---|
| 5,957,866 A | 9/1999 | Shapiro et al. |
| 6,050,950 A | 4/2000 | Mohler |
| 6,478,744 B1 | 11/2002 | Mohler |
| 6,572,560 B1 | 6/2003 | Watrous et al. |
| 6,629,937 B1 | 10/2003 | Watrous |
| 6,898,459 B1 * | 5/2005 | Hayek et al. ............... 600/509 |
| 2002/0052559 A1 | 5/2002 | Watrous |
| 2003/0093003 A1 | 5/2003 | Watrous et al. |

* cited by examiner

SYSTEM AND METHOD FOR DIAGNOSING PATHOLOGIC HEART CONDITIONS

CROSS-REFERENCE TO RELATED APPLICATIONS

This application claims the benefit of prior filed co-pending U.S. Provisional Patent Application No. 60/457,726, filed on Mar. 26, 2003.

BACKGROUND OF THE INVENTION

The present invention relates to a system and method for diagnosing pathologic heart conditions based upon heart sound data.

Studies have shown that primary care physicians frequently refer patients to cardiac specialists on the basis of suspicious heart sounds detected by traditional stethoscope auscultation, though a large percentage of these referrals are dismissed by cardiologists as having no pathologic condition. The costs, delays, worry, and administrative burden resulting from these needless referrals could be reduced if the cues that the specialist uses could be incorporated into an algorithm to automatically screen for pathologic heart sounds and murmurs.

Although attempts have been made to automate screening by auscultation, no device is currently available to fulfill this function. Multiple indicators of pathology are nonetheless available from heart sounds and can be elicited using certain signal processing techniques such as time-frequency analysis. Some pathology signals can reliably be detected and classified as pathologic using a portable electrocardiogram and heart sound measurement unit combined with time-frequency based algorithms. Time-frequency decomposition analysis holds promise for extending these results to detection and evaluation of other audible pathologic indicators.

In addition, an automatic screening algorithm would be useful for detecting pathologic heart conditions in settings where a trained professional is not always available, such as pre sports participation physicals, and examinations performed in remote or underserved areas. Furthermore, automated analysis of digitized clinical information such as heart sounds could have major implications for health care delivery systems using telemedicine.

SUMMARY OF THE INVENTION

The present invention comprises a time-frequency diagnostic device and method. The present invention integrates a cardiologist's auscultation expertise, a large and growing set of comprehensive heart sound files, and digital signal processing algorithms.

A method of diagnosing pathologic heart conditions in which a time series of heart sounds and ECG peaks is filtered and parsed into a sequence of individual heart cycles. A systolic interval as well as systolic sub-intervals are identified for each heart cycle.

The systolic intervals are then digitally filtered to optimize for click detection. A digital filter transform output is then fed to multiple processes that occur for each heartcycle including determining the systole time limits, inputting the time series of the transformed heartsound output to a Neyman-Pearson "constant false alarm rate" (CFAR) detector to identify anomalously high transform coefficients, and creating a vector of detections vs. time. The series of anomalously high detections (one series for each heart cycle) are then assembled into a matrix. Each heart cycle in the matrix is convolved with an averaging vector whose averaging length is consistent with an observed spread of click occurrence times in a database of patients. A click score is then determined from these averaged detections as the maximum element of the vector formed by the median transform coefficient amplitude across heart cycles squared at each time sample multiplied element-wise by the vector formed by the sum across heart cycles of the number of detections at each time sample.

The click score is compared to a threshold value set by a desired probability of detection vs. a probability of false alarm tradeoff. If the click score is less than the threshold then a "no click" indicator is displayed. If the click score is greater than the threshold then a "click present" indicator is displayed. The click score of the patient in question is compared to the distribution of scores of known pathologic cases and known non-pathologic cases from the database. The ranking of the current score in the distribution of pathologic and non-pathologic scores is presented to the operator for additional interpretation context.

The system for diagnosing pathologic heart conditions is comprised of a portable computing device that manages data collection and stores data collected from new patients, and analyzes data. Also included is a patient data collection unit, communicable with the portable computing device, for acquiring and digitizing electro-cardiogram (ECG) and heart sound data from a patient. The patient data collection unit is comprised of a pair of transducer contact microphones (primary and reference) for obtaining acoustic data. Also included is a pair of acoustic pre-amplifiers connected with the transducers. The pre-amplifiers have a passband of 20 Hz to 2 kHz and are used to condition acoustic data received from the contact microphones. Variable amplifiers connected with the acoustic pre-amplifiers variably amplify the conditioned acoustic data. Moreover, several electro-cardiogram (ECG) electrodes connected to an ECG amplifier record ECG data. The acoustic and the ECG data are passed to an analog to digital converter connected with the variable amplifiers and the ECG amplifier. The data is digitized and sent to the computing device for processing by a screening algorithm implemented by the steps described in the method above.

BRIEF DESCRIPTION OF THE DRAWINGS

FIG. 1 illustrates a plot of time-frequency analysis at various scales a.

DESCRIPTION OF THE PREFERRED EMBODIMENTS

Before describing the present invention it is helpful to have a basis for the detection of pathological heart conditions. Analysis of a variety of heart sounds and corresponding diagnoses from the Johns Hopkins School of Medicine (JHU/SOM) has shown that time-frequency analysis is a versatile technique for detecting and classifying pathologic heart conditions. Of the available time-frequency techniques, wavelets are a useful method for representing heart sound frequency dynamics without creating cross term artifacts. Wavelet transforms can be computed for a continuous or discrete set of transform variables, depending on the priority for compactness (e.g., data compression applications) or ease of visual interpretation (e.g., pattern recognition applications), respectively. While compressibility is of interest for future applications, the relative ease of interpretation provided by continuous wavelet transforms (CWTs) suggested their use with the present invention. While wavelet transform analysis are illustrated herein as a preferred method for analyzing heart sound data, frequency based Fourier transform analysis may also be implemented by one of ordinary skill in the art in order to analyze heart sound data.

The CWT of a time series, f(t), is defined as:

$$W(a, b) \equiv \int_{-\infty}^{\infty} f(t) \frac{1}{\sqrt{|a|}} \psi^* \left( \frac{t-b}{a} \right) dt \quad \text{(Equation 1)}$$

where f and ψ are both square-integrable, a is a time scaling variable, and b is a time translation variable. This can also be written as a convolution:

$$W(a,b) = f(b) * \psi^*_{a,0}(-b)$$

where $$\psi_{a,b}(t) \equiv \frac{1}{\sqrt{|a|}} \psi \left( \frac{t-b}{a} \right)$$

While it is possible to construct a ψ to yield an optimal peak (compact, high amplitude) in W for a given f, it would not be guaranteed to be optimal for a different time series g. Since the present invention is to be applied to a variety of heart sound signals, a custom wavelet was not implemented. Rather, the alternative was to draw ψ from a pool of wavelets designed to have various advantageous properties. Wavelet transformations known as second order "coiflets" were implemented with the present invention. It is important to note, however, that other wavelet transformations, including custom wavelets, may be implemented without departing from the spirit or scope of the present invention.

Figure 1:
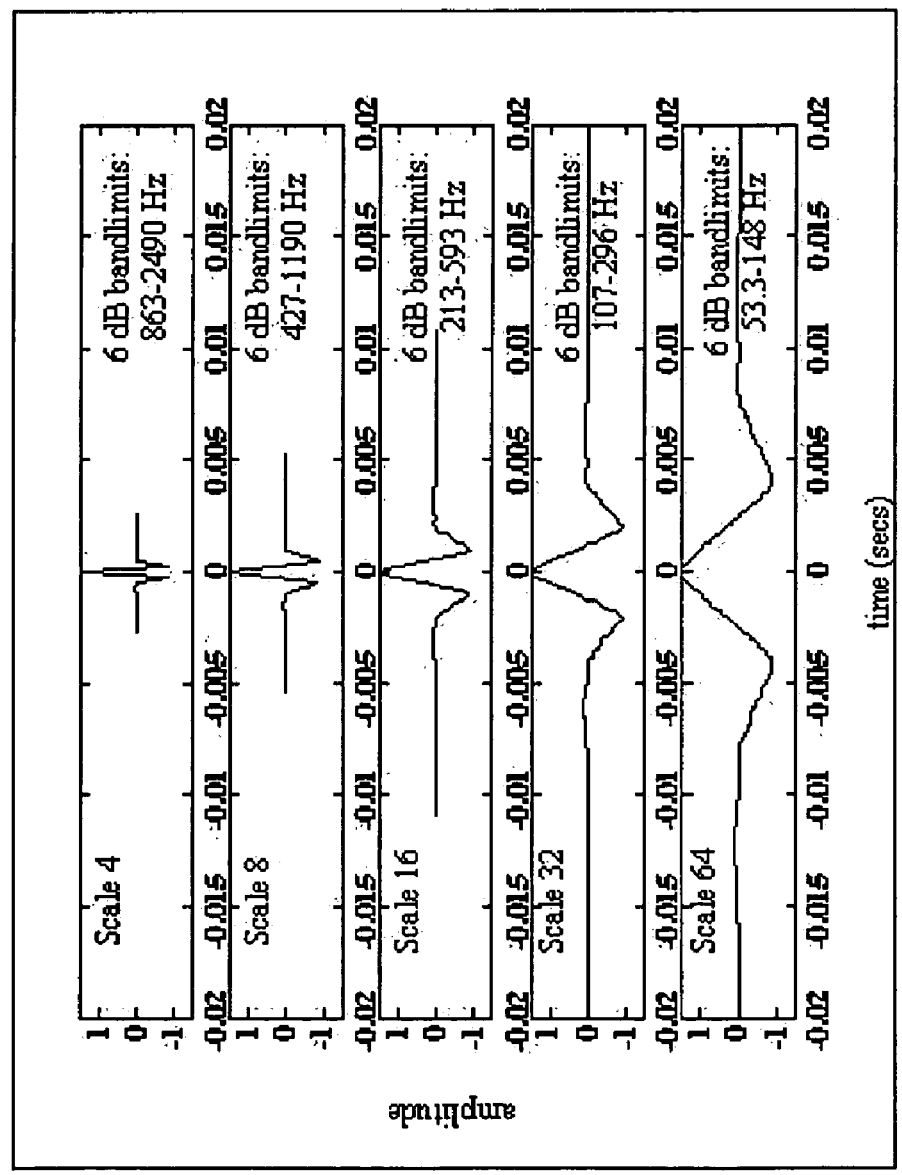

Coiflets of order 2 at various scales, a, are plotted in FIG. 1. The frequency bandpass limits at each scale are given. Due to the equivalence of convolution in the time domain and multiplication in the frequency domain equation 1 shows that the Fourier transform of ψ will act as a bandpass filter of the signal f. The bandpass limits in FIG. 1 are the 6 dB passband frequency limits of the Fourier transform of φ. Wavelets are constructed so as to maintain a constant ratio of center frequency to 3 dB bandwidth (Q), and have a finite duration. Their time-frequency resolution is inherent in their design and scale parameters. This is in contrast to Fourier decomposition, which uses the infinite time extent sine and cosine functions. Time resolution is not inherent in the Fourier transform, but is introduced by the user via windowing the data. Multiple Fourier transforms using distinct window intervals would be required to produce the constant Q decomposition offered by wavelets.

Figure 2:
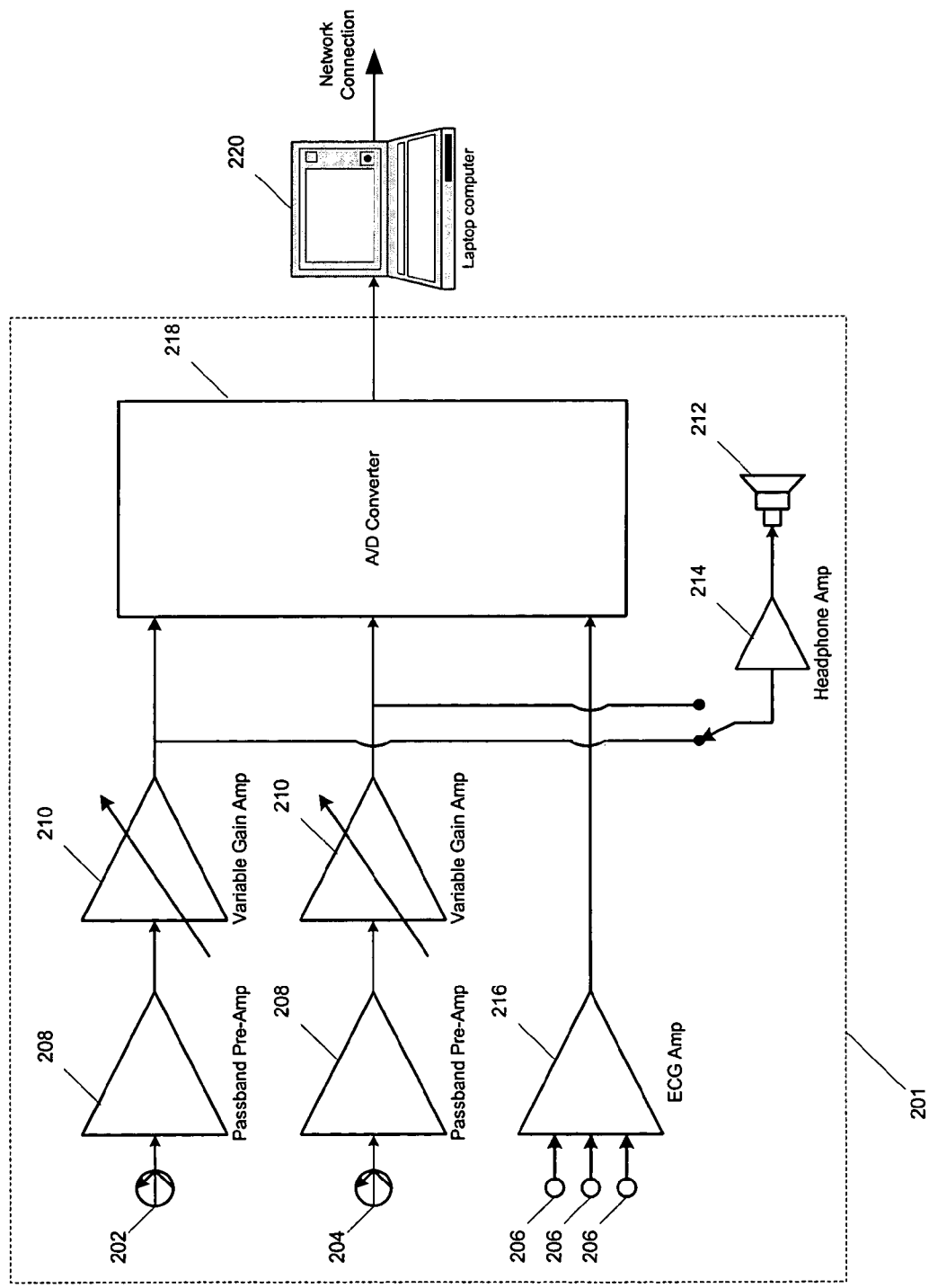
FIG. 2 illustrates a block diagram of system hardware.

A system block diagram of the present invention is illustrated in FIG. 2. The system is comprised of two principal elements. One is a patient data collection unit 201. The other is a computer processing device 220 including or having access to data storage devices. The patient data collection unit performs several functions including obtaining heart sound data via a set of contact microphones in the form of transducers. Two channels of acoustic data are obtained from a patient using a primary transducer 202 and a reference transducer 204. In addition, a set of ECG electrodes 206 are used to obtain electro-cardiogram data from the patient.

The two contact microphones are each conditioned by a pre-amplifier 208 having a passband of 20 Hz to 2 kHz and variable gain amplification stage 210. A set of headphones 212 connected to a headphone amplifier 214 can be used to listen to the acoustic data gathered from the primary transducer 202 and the reference transducer 204. The ECG electrodes 206 feed into an ECG amplifier 216. Outputs from the variable gain amplifiers 210 and the ECG amplifier 216 are fed to a analog-to-digital converter where the acoustic and ECG signals are digitized and recorded. A 12-bit National Instruments PCMCIA analog-to-digital converter is used, for instance, to collect and digitize data at a rate (e.g. 8.13 kHz) consistent with the highest data frequencies of interest.

Once the signals have been digitized and recorded, the patient data collection unit 201 forwards the data to a computer processing device 220. The computer processing device 220 is typically a laptop computer (due to its compact transportable nature) having adequate data storage capacity. However, the patient data collection unit 201 may be connected to other computer processing devices without departing from the spirit or scope of the present invention. A computer software program accesses heart sound data that has either been collected and forwarded by the patient data collection unit 201, or is resident on the laptop computer 220, or can be obtained from another source of heart sound data.

The computer program applies a screening algorithm to the heart sound data in order to determine whether the heart sound data is to be classified as normal or pathologic. Each heart sound data file corresponds to a different patient. When the algorithm has operated on the heart sound data that has been input, the computer program will display the results on a display screen to the doctor, nurse, or technician operating the computer. Results indicating a pathologic condition will likely cause the patient to be referred to a cardiologist for further examination. Otherwise, a cardiologist referral can be deemed unnecessary.

Figure 3:
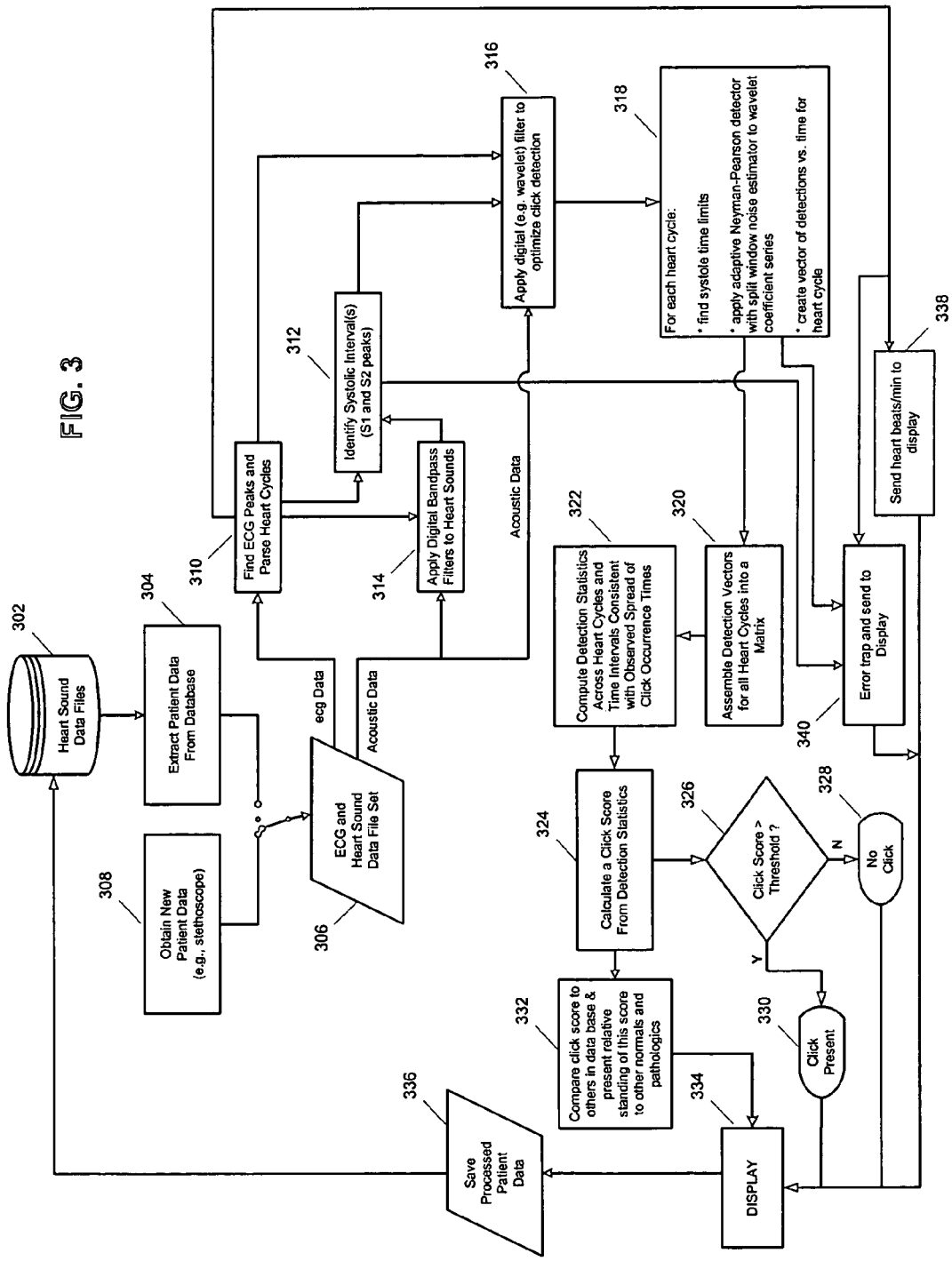
FIG. 3 illustrates a logic flow diagram of the processes used to diagnose pathologic heart conditions such as heart clicks.

FIG. 3 illustrates the flow of logic and processing that occurs in the various elements described in FIG. 2. Digitized heart sound recordings were collected on patients in the Pediatric Cardiology Echocardiography Laboratory in the Johns Hopkins Outpatient Center. The recordings were stored in a Heart Sound database 302. Recorded heart sounds could then be extracted 304 from the heart sound database 302 and placed into an ECG/heart sound data file set 306. Alternatively, ECG and heart sound data could be obtained directly from a patient 308 and placed into the ECG/heart sound data file set 306. The ECG/heart sound data file set 306 serves as the data to be fed to a screening algorithm. The purpose of the screening algorithm is to analyze the ECG data and heart sound data in order to detect pathologic anomalies that may be present. Thus the system is to be used as a diagnostic aid. In order for the screening algorithm to be applied, the data set must first be manipulated. Initially, the ECG data and acoustic heart sound data are separated. The ECG data is used to parse the time series into a sequence of individual heart cycles via a process that identifies the ECG peaks 310.

A systolic interval is then identified 312 for each heart cycle. The first and second heart sounds are identified both by reference to the heart cycle boundaries and acoustically using a passband of 25–140 Hz 314. In the acoustic method the times of the acoustic maxima define systole and diastole. Systole can then be divided into various sub-intervals including, but not limited to, the first half of the systolic interval, the total systolic interval, the middle half of the systolic interval, and the last half of the systolic interval. A short interval to isolate the first and second heart sounds is factored in. Then, the acoustic heart sound data is passed through a digital bandpass filter 316, in this case a second order coiflet CWT transform. The purpose of this filter is to optimize the acoustic data series for click detection. The digital wavelet filter output of box 316 is then fed to multiple processes that occur for each heartcycle 318.

For each heartcycle 318, the systole time limits are determined, a time series of the transform at specific wavelet scales (16 and 24 for instance) are input to a Neyman-Pearson "constant false alarm rate" (CFAR) detector to identify anomalously high wavelet coefficients, and a vector of detections vs. time is created. The noise model for the Neyman-Pearson CFAR detector is statistically based on the study of heart sound wavelet coefficients in a variety of patients. It was determined to be best fit by a gamma distribution.

The series of anomalously high detections (one series for each heart cycle) are then assembled into a matrix 320. The matrix is convolved with an averaging vector, whose length is derived from the expected time spread of click occurrence yielding detection statistics across heart cycles and time intervals consistent with an observed spread of click occurrence times 322. A click score is then calculated 324. The click score is determined as the maximum element of the vector formed by the median wavelet coefficient amplitude across heart cycles squared at each time sample multiplied element-wise by the vector formed by the sum across heart cycles of the number of detections at each time sample.

The click score is fed to a decision box 326 in which it is compared to a threshold value. The threshold value is set by a desired probability of detection vs. a probability of false alarm tradeoff. If the click score is less than the threshold then a "no click" indicator 328 is displayed 334. If the click score is greater than the threshold then a "click present" indicator 330 is displayed 334.

In addition, the click score is compared to other click scores in a database and the newly calculated click score is presented 332 relative to other click scores that are both normal and pathologic. The newly calculated click score and all the corresponding data that led to its calculation is saved in a patient database 336. The patient database continues to grow and provide greater reliability and accuracy as it becomes populated with more and more samples.

As the data is being processed certain conditions are monitored 338, 340 by the present invention to indicate whether there is an error in processing. The error conditions presently monitored include: a) that the ecg data allows parsing of the heartcycles; b) reasonable values are obtained for S1 and S2 peak location; and c) that the length of systole is enough to contain the split window used for the CFAR processor.

There are several advantages realized by the present invention. An automatic screening algorithm would be useful for detecting pathologic heart murmurs in settings where a trained professional is not always available, such as pre sports participation physicals, and examinations performed in remote or underserved areas. Furthermore, automated analysis of digitized clinical information such as heart sounds could have major implications for health care delivery systems using telemedicine.

Automated analysis of heart sound data could also be used by cardiologists to quantitatively follow and document changes in severity of certain conditions such as aortic stenosis and mitral regurgitation, in which changes in murmur characteristics are known to correlate with changes in disease severity. In addition, since data for analysis could theoretically be collected using any electronic stethoscope, home care nurses or nurses aides could make inexpensive in-home bedside recordings that could be analyzed later to monitor changes in certain conditions as reflected in heart sounds.

It is to be understood that the present invention illustrated herein is readily implementable by those of ordinary skill in the art as a computer program product having a medium with computer program(s) embodied thereon. The computer program product is capable of being loaded and executed on the appropriate computer processing device(s) in order to carry out the method or process steps described. Appropriate computer program code in combination with hardware implements many of the elements of the present invention. This computer code is typically stored on removable storage media. This removable storage media includes, but is not limited to, a diskette, standard CD, pocket CD, zip disk, or mini zip disk. Additionally, the computer program code can be transferred to the appropriate hardware over some type of data network.

The present invention has been described, in part, with reference to flowcharts or logic flow diagrams. It will be understood that each block of the flowchart diagrams or logic flow diagrams, and combinations of blocks in the flowchart diagrams or logic flow diagrams, can be implemented by computer program instructions.

These computer program instructions may be loaded onto a general purpose computer, special purpose computer, or other programmable data processing apparatus to produce a machine, such that the instructions which execute on the computer or other programmable data processing apparatus create means for implementing the functions specified in the flowchart block or blocks or logic flow diagrams.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart blocks or logic flow diagrams. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart blocks or logic flow diagrams.

Accordingly, block(s) of flowchart diagrams and/or logic flow diagrams support combinations of means for performing the specified functions, combinations of steps for performing the specified functions and program instruction means for performing the specified functions. It will also be understood that each block of flowchart diagrams and/or logic flow diagrams, and combinations of blocks in flowchart diagrams and/or logic flow diagrams can be implemented by special purpose hardware-based computer systems that perform the specified functions or steps, or combinations of special purpose hardware and computer instructions.

In the following claims, any means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

The invention claimed is:

1. A method of diagnosing pathologic heart conditions comprising:
   parsing a time series of heart sounds into a sequence of individual heart cycles;
   determining the systolic interval of the heart cycles;
   identifying a subinterval for each systolic interval of the heart cycles;
   filtering the time series of heart sounds using a time-frequency transformation;
   identifying anomalously high wavelet coefficients using a constant false alarm rate (CFAR) detector;
   assembling the series of anomalously high detections into a matrix;
   convolving the matrix with an averaging vector, said vector's length derived from the expected time spread of a click occurrence, the convolution yielding detection statistics across heart cycles and time intervals consistent with an observed spread of click occurrence times;
   calculating a click score as the maximum element of a vector formed by the median wavelet coefficient amplitude across heart cycles squared at each time sample multiplied element-wise by a vector formed by the sum across heart cycles of the number of detections at each time sample; and
   comparing the click score to a threshold level in order to distinguish between a normal heart and a pathologic heart.

2. The method of claim 1 further comprising ranking the click score relative to other click scores in a database to establish its standing amongst a population of other click scores of known pathologic and non-pathologic hearts.

3. The method of claim 1 wherein parsing the time series of heart sounds into a sequence of individual heart cycles uses electro-cardiogram (ECG) data to transform a time series of heart sounds into a sequence of individual heart cycles.

4. The method of claim 1 wherein parsing the time series of heart sounds into a sequence of individual heart cycles uses acoustic heart sounds obtained directly from a patient to transform a time series of heart sounds into a sequence of individual heart cycles.

5. The method of claim 1 wherein determining the systolic interval of the heart cycles is achieved by identifying pulses on an electro-cardiogram (ECG).

6. The method of claim 1 wherein determining the systolic interval of the heart cycles is achieved by acoustically locating a first and a second heart sound using a bandpass filter, said bandpass filter applied to the time series of heart sounds.

7. The method of claim 1 wherein the systolic sub-interval is centered in the systolic interval.

8. The method of claim 1 wherein the systolic sub-interval is centered in systole and spans half of the systolic interval.

9. The method of claim 1 wherein filtering the time series of heart sounds using a time-frequency transformation is implemented by a second order coiflet continuous wavelet transform (CWT).

10. The method of claim 1 wherein filtering the time series of heart sounds using a time-frequency transformation is implemented by a Fourier transform.

11. A system for diagnosing pathologic heart conditions comprising:
   means for parsing a time series of heart sounds into a sequence of individual heart cycles;
   means for determining the systolic interval of the heart cycles;
   means for identifying a subinterval for each systolic interval of the heart cycles;
   means for filtering the time series of heart sounds using a time-frequency transformation;
   means for identifying anomalously high wavelet coefficients using a constant false alarm rate (CFAR) detector;
   means for assembling the series of anomalously high detections into a matrix;
   means for convolving the matrix with an averaging vector, said vector's length derived from the expected time spread of a click occurrence, the convolution yielding detection statistics across heart cycles and time intervals consistent with an observed spread of click occurrence times;
   means for calculating a click score as the maximum element of a vector formed by the median wavelet coefficient amplitude across heart cycles squared at each time sample multiplied element-wise by a vector formed by the sum across heart cycles of the number of detections at each time sample;
   means for comparing the click score to a threshold level in order to distinguish between a normal heart and a pathologic heart; and
   means for ranking the click score relative to others in a database to establish its standing amongst a population of other scores of known pathologic and non-pathologic cases.

12. The system of claim 11 further comprising means for ranking the click score relative to other click scores in a database to establish its standing amongst a population of other click scores of known pathologic and non-pathologic hearts.

13. The system of claim 11 wherein the means for parsing the time series of heart sounds into a sequence of individual heart cycles uses electrocardiogram (ECG) data to transform a time series of heart sounds into a sequence of individual heart cycles.

14. The system of claim 11 wherein the means for parsing the time series of heart sounds into a sequence of individual heart cycles uses acoustic heart sounds obtained directly from a patient to transform a time series of heart sounds into a sequence of individual heart cycles.

15. The system of claim 11 wherein the means for determining the systolic interval of the heart cycles is achieved by identifying pulses on an electro-cardiogram (ECG).

16. The system of claim 11 wherein the means for determining the systolic interval of the heart cycles is achieved by acoustically locating a first and a second heart sound using a bandpass filter, said bandpass filter applied to the time series of heart sounds.

17. The system of claim 11 wherein the systolic sub-interval is centered in the systolic interval.

18. The system of claim 11 wherein the systolic sub-interval is centered in systole and spans half of the systolic interval.

19. The system of claim 11 wherein the means for filtering the time series of heart sounds using a time-frequency transformation is implemented by a second order coiflet continuous wavelet transform (CWT).

20. The system of claim 11 wherein the means for filtering the time series of heart sounds using a time-frequency transformation is implemented by a Fourier transform.

21. A computer readable medium comprising a computer program for diagnosing pathologic heart conditions, the computer program product comprising:
   computer program code for parsing a time series of heart sounds into a sequence of individual heart cycles;
   computer program code for determining the systolic interval of the heart cycles;
   computer program code for identifying a subinterval for each systolic interval of the heart cycles;
   computer program code for filtering the time series of heart sounds using a time-frequency transformation;
   computer program code for identifying anomalously high wavelet coefficients using a constant false alarm rate (CFAR) detector;
   computer program code for assembling the series of anomalously high detections into a matrix;
   computer program code for convolving the matrix with an averaging vector, said vector's length derived from the expected time spread of a click occurrence, the convolution yielding detection statistics across heart cycles and time intervals consistent with an observed spread of click occurrence times;
   computer program code for calculating a click score as the maximum element of a vector formed by the median wavelet coefficient amplitude across heart cycles squared at each time sample multiplied element-wise by a vector formed by the sum across heart cycles of the number of detections at each time sample;
   computer program code for comparing the click score to a threshold level in order to distinguish between a normal heart and a pathologic heart; and
   computer program code for ranking the click score relative to others in a database to establish its standing amongst a population of other scores of known pathologic and non-pathologic cases.

22. The computer program of claim 21 further comprising computer program code for ranking the click score relative to other click scores in a database to establish its standing amongst a population of other click scores of known pathologic and non-pathologic hearts.

23. The computer program of claim 21 wherein the computer program code for parsing the time series of heart sounds into a sequence of individual heart cycles uses electro-cardiogram (ECG) data to transform a time series of heart sounds into a sequence of individual heart cycles.

24. The computer program of claim 21 wherein the computer program code for parsing the time series of heart sounds into a sequence of individual heart cycles uses acoustic heart sounds obtained directly from a patient to transform a time series of heart sounds into a sequence of individual heart cycles.

25. The computer program of claim 21 wherein the computer program code for determining the systolic interval of the heart cycles is achieved by identifying pulses on an electrocardiogram (ECG).

26. The computer program of claim 21 wherein the computer program code for determining the systolic interval of the heart cycles is achieved by acoustically locating a first and a second heart sound using a bandpass filter, said bandpass filter applied to the time series of heart sounds.

27. The computer program of claim 21 wherein the systolic sub-interval is centered in the systolic interval.

28. The computer program of claim 21 wherein the systolic sub-interval is centered in systole and spans half of the systolic interval.

29. The computer program of claim 21 wherein the computer program code for filtering the time series of heart sounds using a time-frequency transformation is implemented by a second order coiflet continuous wavelet transform (CWT).

30. The computer program of claim 21 wherein the computer program code for filtering the time series of heart sounds using a time-frequency transformation is implemented by a Fourier transform.

* * * * *